(12) United States Patent
Tong et al.

(10) Patent No.: US 7,629,114 B2
(45) Date of Patent: Dec. 8, 2009

(54) METHOD OF COLLECTING NASOPHARYNGEAL CELLS AND SECRETIONS FOR DIAGNOSIS OF VIRAL UPPER RESPIRATORY INFECTIONS AND SCREENING FOR NASOPHARYNGEAL CANCER

(75) Inventors: Sun-Wing Tong, Kowloon (HK); Yi-Wei Tang, Brentwood, TN (US)

(73) Assignee: World Sense Technology Limited, Discovery Bay (HK)

( * ) Notice: Subject to any disclaimer, the term of this patent is extended or adjusted under 35 U.S.C. 154(b) by 745 days.

(21) Appl. No.: 10/923,444

(22) Filed: Aug. 20, 2004

(65) Prior Publication Data

US 2005/0048465 A1  Mar. 3, 2005

Related U.S. Application Data

(60) Provisional application No. 60/497,801, filed on Aug. 26, 2003.

(51) Int. Cl.
*C12Q 1/00* (2006.01)
(52) U.S. Cl. .......................................................... 435/4
(58) Field of Classification Search ........................ None
See application file for complete search history.

(56) References Cited

U.S. PATENT DOCUMENTS

| | | | |
|---|---|---|---|
| 5,869,231 A | 2/1999 | Römisch | |
| 2002/0142294 A1* | 10/2002 | Blair et al. | 435/5 |
| 2003/0134293 A1* | 7/2003 | Liu | 435/6 |

OTHER PUBLICATIONS

Scruggs, J., Wallace, T., and Calvin, H., Route of Absorption of Drug and Ointment After Application to the Eye, Ann Ophthalmol. Mar. 1978;10(3):267-71.*
Sahlin S, Chen E., Gravity, blink rate, and lacrimal drainage capacity, Am J Ophthalmo. 1997 124-758-764.*
Austen, D., Lacrimal dilation and syringing, Optometry Today, Feb. 26, 1999, 29-32.*
Ukkonen P.; Julkunen I., Preparation of nasopharyngeal secretions for immunofluorescence by one-step centrifugation through Percoll, Journal of Virological Methods, 1987, vol. 15: 291-301.*
McIntosh K.; McQuillin J.; Reed S.E.; Gardner P.S., Diagnosis of human coronavirus infection by immunofluorescence: Methodand application to respiratory disease in hospitalized children, Journal of Medical Virology, 1978, vol. 2: 341-346.*
Basky, G., Accurate test for nasopharyngeal cancer developed by Canadian researchers, Canadian Medical Association Journal, Jul. 27, 1999, 161(2):125.*
T. R. Tong, "Conjunctiva-Upper Respiratory Tract Irrigation for Early Diagnosis of Severe Actute Respiratory Syndrome", *Journal of Clinical Microbiolody*, Nov. 2003, p. 5352, vol. 41, No. 11.
T. R. Tong, "An Alternative Method of Procuring Nasopharyngeal Specimens for SARS Coronavirus and Influenza Virus Detection", Hong Kong SARS Forum and Hospital Authority Convention 2004, May 8-11, 2004.
BJO, eLetters for Loon et al., 88 (7) 861-863, (2004 ).
J. S. M. Peiris, et al., "Coronavirus as a Possible Cause of Severe Acute Respiratory Syndrome", The Lancet, vol. 361, Apr. 19, 2003, pp. 1319-1325.
T. Kulken et al., "Newly Discovered Coronavirus as the Primary Cause of Severe Acute Respiratory Syndrome", The Lancet, vol. 362, Jul. 26, 2003, pp. 263-270.
J. S. M. Peiris, et al., "Clinical Progression and Viral Load in a Community Outbreak of Coronavirus-Associated SARS Pneumonia: a Prospective Study", The Lancet, pp. 1-6, (2003).
D. M. Musher, M.D., "How Contagious Are Common Respiratory Tract Infections", *The New England Journal of Medicine*, 348: 13, pp. 1256-1266, Mar. 27, 2003.
Vaccine Science, http://www.sabin.org/vaccine_science_polio.htm, pp. 1-3, (2004).
S. C. Loon et al., "The Severe Acute Respiratory Syndrome Coronavirus in Tears", *Br J. Ophthalmol*, 2004; 88: 861-863, (2004).
W. M. Chan, et al., "Tears and Conjunctival Scrapings for Coronavirus in Patients with SARS", *Br J. Ophthalmol*, 2004, 88:968-977.

* cited by examiner

*Primary Examiner*—Gary B Nickol
*Assistant Examiner*—Nicole Kinsey White
(74) *Attorney, Agent, or Firm*—Cohen Pontani Lieberman & Pavane LLP

(57) ABSTRACT

The present invention provides a method of collecting nasopharyngeal specimens by introducing physiologic solution into the conjunctival sacs and collecting the irrigate that drains into the oroharynx. The invention further provides a kit to facilitate such a method. The present invention also provides a method of delivering a biological active to the eyes, nasal, nasopharyngeal, and oropharyngeal regions.

3 Claims, 7 Drawing Sheets

Lateral wall of the left half of the nasal cavity and nasopharynx. In the lower figure parts of the conchae have been removed to show the openings of the sinuses and the nasolacrimal duct.

Fig. 4

Instructions to patients on method of collecting CURTI (Conjunctivo-Upper Respiratory Tract Irrigation)

English version:

Wash hands. Semi-recline on a couch or bed.
Gently massage both lacrimal sacs (see position in figure indicated by "x").

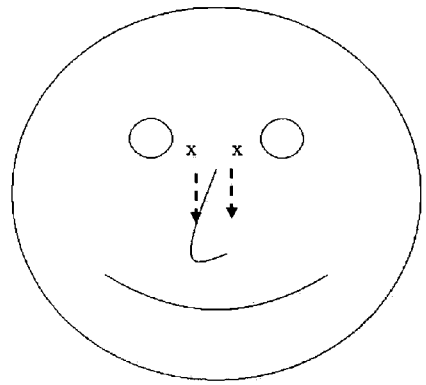

Apply one drop of sterile normal saline eye-drops (provided) into each conjunctival sac (eye), just like applying eye-drops. Do not apply too much as it will spill. You may gently massage the lacrimal sacs again. Blinking your eyes will help the fluid enter your lacrimal sac. Do not forcibly shut your eyelids, as this will cause the fluid to spill.

The applied saline solution will run into the nose through the nasolacrimal ducts (indicated by dotted arrows in figure), and then into the oropharynx through the nose and nasopharynx. DO NOT SWALLOW the liquid. Collect it in the throat. It is better to not immediate spit it out but to continue with applying more eyedrops until the urge to swallow is overwhelming. This ensures that the specimen is not mixed with too much saliva.

Gently spit it into the provided specimen bottle. Your spit should taste salty.

Repeat steps 3-5 for as many times as it takes to supply 2 ml of sample, or until the eye drops are used up.
Replace the cover on the specimen bottle.
Alert nursing staff that the specimen is ready for collection.

Fig. 4 (cont'd)

NOTE: There is a time lag of up to 5 minutes between application of eye drops and the feeling of fluid collecting in your throat. In addition, after using up the eye drops, fluid will continue to collect in your throat for up to 1-2 minutes. Please also collect that in the specimen container.

SUMMARY: Apply eye-drops, blink eyes, spit out the fluid that collects in your throat into the provided container.

Fig. 5A

CURTI Results of 52 Influenza A

|  | Number (positive/total) | Percent % |
| --- | --- | --- |
| DIF | 22*/52 | 42 |
| Viral culture (VC) | 12/21 | 47 |
| DIF or VC | 26/52 | 50 |

\* 5 cases have abundant positive cells (age 53-80)

METHOD OF COLLECTING NASOPHARYNGEAL CELLS AND SECRETIONS FOR DIAGNOSIS OF VIRAL UPPER RESPIRATORY INFECTIONS AND SCREENING FOR NASOPHARYNGEAL CANCER

RELATED APPLICATIONS

This application claims priority from U.S. Provisional Patent Application Ser. No. 60/497,801 which was filed on Aug. 26, 2003.

FIELD OF THE INVENTION

This application claims priority from U.S. Provisional Patent Application Ser. No. 60/497,801 which was filed on Aug. 26, 2003.

Invasive medical diagnosis involves the insertion of medical instruments into a patient's body through a natural orifice or the skin or mucosa, with or without the procurement of body fluid, exfoliated cells, blood or tissue.

This invention comprises a non-invasive procurement of cells, such as exfoliated upper respiratory tract epithelial cells, or other cell types, foreign or host, benign or malignant, present in the upper respiratory secretions, including viruses, molecules and macromolecules, for medical diagnosis and scientific studies. The invention further provides an effective method of delivering biological actives to the nasal, nasopharyngeal, and oropharyngeal regions.

BACKGROUND OF THE INVENTION

Traditionally, the diagnosis of upper respiratory tract viral infection was based on clinical history and examination, and did not include laboratory studies, because such studies have a long turn-around time and have little impact on patient management.

Recently, however, antibody-based and nucleic-acid based laboratory studies have significantly shortened the turn-around time of laboratory investigations to the point that clinical management, particularly decisions on quarantining and cohorting patients, can be positively affected. The recent SARS (Severe Acute Respiratory Syndrome) epidemic has heightened the need for a rapid diagnostic method.

The points of entry of most viral upper respiratory illnesses are the eyes, nose and mouth; the virus frequently gains an initial foothold in the nasopharynx and sometimes the conjunctiva or possibly the nasolacrimal system. Subsequent to the infection of susceptible hosts, viral replication takes place in the host's epithelial cells, causing release of more infectious virus particles into the secretions. Often, the infected epithelial cells detach from the epithelial lining, and can be collected for identification of the virus. Viral particles are also shed into the extracellular space by active secretion or excretion or upon death of the virally infected cells. Methods used to detect virus or virally infected cells include viral culture, direct immunofluorescent microscopy, a variety of immunoassays, and nucleic acid-based diagnostic tests.

Whereas the incidence of uterine cervical carcinoma is greatly reduced in countries with effective cervical cytology screening programs, incidence of nasopharyngeal carcinoma is not affected, as there is no available means of non-invasively or minimal-invasively obtaining cells for exfoliative cytological cancer screening.

PRIOR ART

The current gold standard method of harvesting virally infected upper respiratory epithelial cells is by nasopharyngeal aspiration. This method involves the instillation of a sterile electrolyte solution via a plastic cannula into the nasopharynx, and the recovery of the fluid by aspiration into a trap bottle using negative pressure. Patients dislike the procedure because it is irritating or painful, and staff dislike it because it causes sneezing and coughing, thereby posing danger of infectious disease. Variations of the technique include aspiration without instillation of electrolyte solution, and washing with a proprietary nasopharyngeal wash collection device.

For example, U.S. Pat. No. 5,643,202 describes a self-contained manual device designed for irrigation and collection of nasopharyngeal secretions. The device is expensive, and the method poses the risk of provoking sneezing and coughing.

A similar method practiced in some institutions that does not use the above device consists of pushing 10-15 ml of physiologic saline into one nostril and collecting fluids coming out from the other nostril. It is not comfortable for the patient and is potentially dangerous to the personnel, as explained above.

Other less effective methods of procuring nasopharyngeal specimens include insertion of a cotton-tipped swab into the nasopharynx through the nose (nasopharyngeal swab), nose swab, nose irrigation, throat swab, oral gargle, and collection of saliva.

All of the above methods therefore have disadvantages which result in inadequate clinical specimens, patient discomfort, or danger to medical personnel, as further explained in detail below.

Inadequate Clinical Specimen:

For laboratory test results to be useful to clinicians, the sensitivity (positivity in the presence of disease) and specificity (negativity in the absence of disease) of the tests must be high. The standard is affected by factors including the ability to procure a representative specimen, and the laboratory technology employed. An inadequate clinical specimen therefore compromises the overall sensitivity and specificity of a laboratory test.

In the case of viral upper respiratory infections, the diagnostic material is often virally infected, exfoliated upper respiratory ciliated columnar epithelial cells, or extracellular viral particles, capsid protein or nucleic acid. The gold standard procedure for collecting this type of specimen has been the nasopharyngeal aspirate, because of the direct procurement of such cells by washing through a cannula positioned at the surface of the nasopharynx.

Nasopharyngeal swab also procures material directly from the nasopharynx. However, the number of cells that attach to the swab and can be subsequently recovered for diagnostic tests is limited.

Nose swab involves the swabbing of the anterior nasal cavity, short of the nasopharynx, and represents a compromise of the specimen quality for reduced patient discomfort. Often, this is the only option for children, who will not cooperate sufficiently for nasopharyngeal aspiration or swab unless heavily sedated.

Saliva and throat swab represent similar compromises. Throat swab might permit the recovery of a small amount of nasopharyngeal cells if properly performed. This is because exfoliated nasopharyngeal cells eventually enter the gastrointestinal tract through the throat. Saliva, however, is unsatisfactory because most of the saliva comes from the three paired salivary glands (parotid glands, submandibular glands, and sublingual glands), which empty their contents into the anterior oral cavity. The saliva that a person spits out makes no contact with the secretions at the back of the throat. Sputum and secretions from the back of the throat are different from saliva, and cannot usually be brought out unless the patient has excessive secretions from the lower respiratory tract or the nasopharynx and back of the throat. Throat gargle may bring the gargling fluid into contact with the secretions at the back of the throat. However, the soft palate is competent in most individuals, thereby preventing reflux of the gargling fluid into the nasopharynx. Also, gargling might cause coughing (see below). The number of cells recovered by gargling is therefore limited and further diluted by the gargling fluid.

Recently, the coronavirus SARS-CoV that causes severe acute respiratory syndrome (SARS) has been recovered from lacrimal secretions (tear). However, a different institution reports the inability to isolate the virus from a variety of specimens taken from the eyes, including tear, suggesting that procurement of tear by ophthalmologists is not an efficient method for virological diagnosis. In addition, procurement of tear for the diagnosis of SARS requires the service and exposure of ophthalmologists to potentially infectious patients and the use of special equipments that may not be available at many health care centers.

Patient Discomfort:

With the exception of collection of saliva, all of the existing methods involve mild to significant patient discomfort, ranging from mild irritation to pain. Some methods, such as nasopharyngeal aspiration, cannot be performed in children or uncooperative patients without sedation.

Danger to Medical Personnel:

Many methods outlined above cause irritation of the nose, resulting in sneezing. Gargling often causes coughing because of inadvertent aspiration of fluid into the larynx. Sneezing and coughing protects the patient by forceful ejection of noxious stimulants. However, these activities also produce aerosols laden with infectious organisms, which pose a real threat to medical personnel collecting such specimens. Even the procurement of tear involves close contact between a potentially infectious source patient and the medical personnel performing the procedure. While illnesses like influenza A can be prevented to a certain extent by immunization of the medical personnel, diseases like SARS and other emerging infectious diseases, which have no available vaccine and are associated with a substantial mortality rate, present grave risks.

Nasopharyngeal carcinoma has no available cytological or molecular screening because nasopharyngeal specimens are difficult to obtain or solicit for the purpose of cancer screening. Diagnosis is performed using endoscopic visualization and biopsy.

SUMMARY OF THE INVENTION

This invention allows for the procurement of exfoliated nasopharyngeal cells and secretions by introducing physiologic normal saline solution into the conjunctival sacs, followed by the collection of the irrigate and rehydrated secretions that drain into the oropharynx through the nasolacrimal ducts, nose and nasopharynx. Generally, patients can collect the irrigate in the pharynx and spit it into a specimen container, without swallowing it. The specimen can then be processed for clinical laboratory diagnosis or scientific studies.

This invention combines several advantages, such as sampling of all three portals (eyes, nose and mouth) of entry of upper respiratory viral pathogens, self-procurement without risking medical personnel; reduction of risk of contaminating the hospital or clinic environment or nosocomial infection of other patients or staff via contaminated aerosol; reduced patient discomfort; satisfactory yield of nasopharyngeal material; and no undue dilution of the secretions by irrigate fluid. When used as part of a kit, the procedure can be performed in the patient's own home or in an isolation or quarantine facility. Because this invention is without discomfort or side-effect, it is more readily repeated, either immediately to give more specimens for other studies, or at a later date, for longitudinal studies, such as changes in viral load during disease evolution or in response to therapy.

This invention also provides for a means to initiate a program to screen for nasopharyngeal cancer in locations where it is prevalent. This invention also provides for an effective method of delivering biological actives to the eyes, upper respiratory tract and the body as a whole through the gastrointestinal tract.

Definitions

"Ribonuclease" means any of a variety of a widely distributed type of enzymes that cleaves RNA.

"Deoxyribonuclease" means an endonuclease with preference for DNA. Endonucleases are enzymes that cleave nucleic acids at certain positions, cutting the chain. Some act on both RNA and DNA.

"Nosocomial infection" means the spread of an infectious disease from patient to patient within a hospital or health care facility.

"Polymerase chain reaction (PCR)" refers to an in vitro technique for making many copies of a stretch of DNA sequence. It employs repetitive thermal cycling consisting of denaturation of double-stranded DNA, annealing of appropriate oligonucleotide primers, and extension of the primer by polymerase enzyme.

"RT-PCR (reverse transcriptase polymerase chain reaction)" is a type of PCR in which the starting template is RNA, where reverse transcriptase is used to make a DNA template. Some thermostable polymerases have appreciable reverse transcriptase activity; however, it is more common to perform an explicit reverse transcription, inactivate the reverse transcriptase or purify the product, and then conventional PCR separately.

"Enzyme immuno-assay (EIA)" means a diagnostic system (often packaged as a small portable kit) based on the specificity of an antigen-antibody reaction, and employing the catalytic activity of enzymes on substrates as a means for signal amplification and detecting of an antigen-antibody reaction.

"Microsatellites" are short sequences of di- or trinucleotide repeats of variable length distributed widely throughout the genome.

"Telomere" is the end of a chromosome.

"Telomerase" is a DNA polymerase with the rather unusual ability to selectively elongate oligonucleotides from the telomere. The enzyme contains an essential 159 residue RNA sequence that provides a template for the replication of the G-rich telomere sequences.

"Promoter" is a region of DNA that RNA polymerase binds to before initiating the transcription of DNA into RNA.

BRIEF DESCRIPTION OF THE DRAWINGS

In the drawings:

FIG. 4 depicts the English version of the patient instruction sheet for collecting CURTI specimens.

DETAILED DESCRIPTION OF THE DRAWINGS

Figure 1:
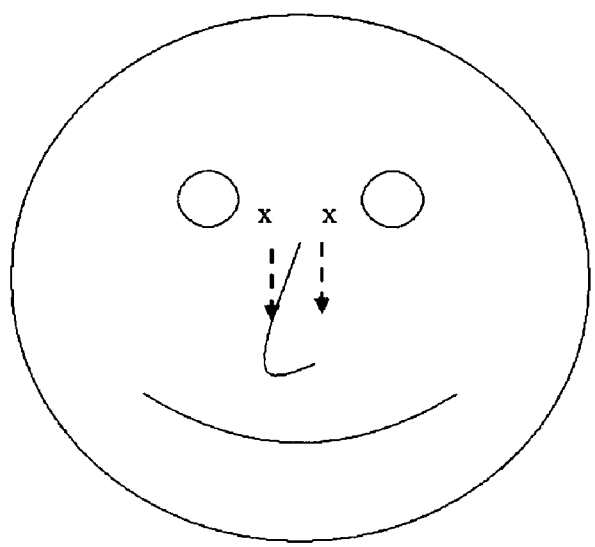
FIG. 1 depicts the direction of flow of the irrigate from eyes to nose.

FIG. 1 depicts the route of drainage of physiological saline from the conjunctival sacs to the nasal cavities.

Figure 2:
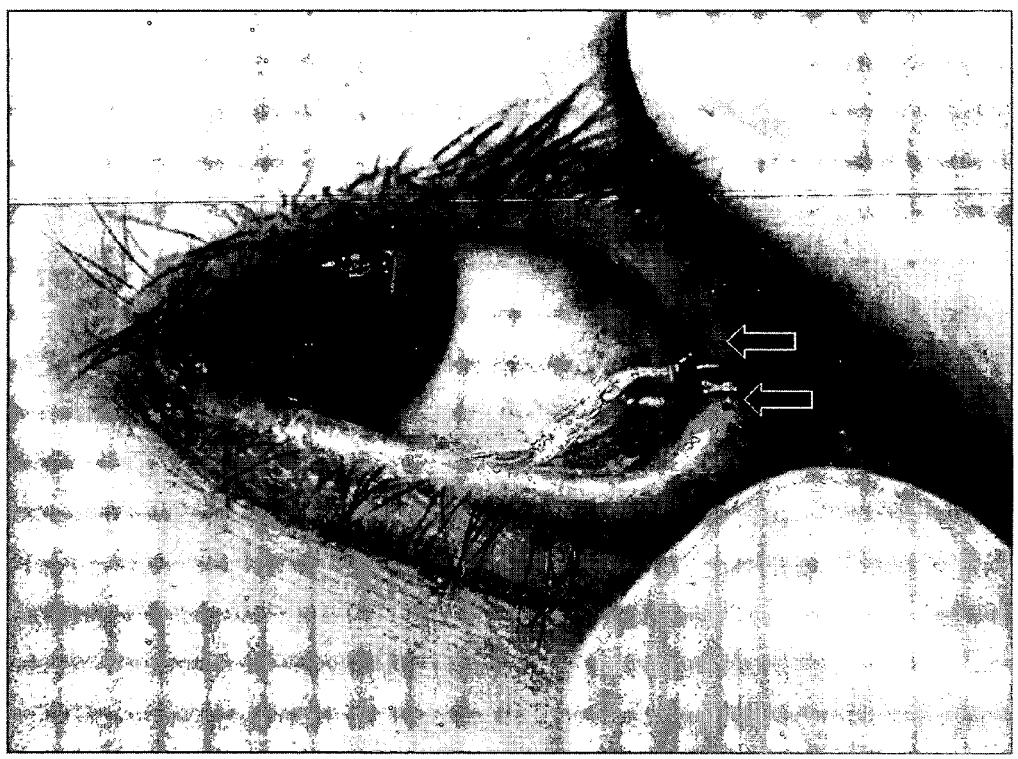
FIG. 2 depicts the site of entry of fluid into the lacrimal sac.

FIG. 2 shows a photograph of the right eye. The eyelids are spread open to reveal the normally inward-pointing lacrimal puncta, one on each eyelid. They are located atop a small papilla (nipple-like projection) on the medial aspect (near the nose bridge) of the eyelid (block arrows).

Figure 3:
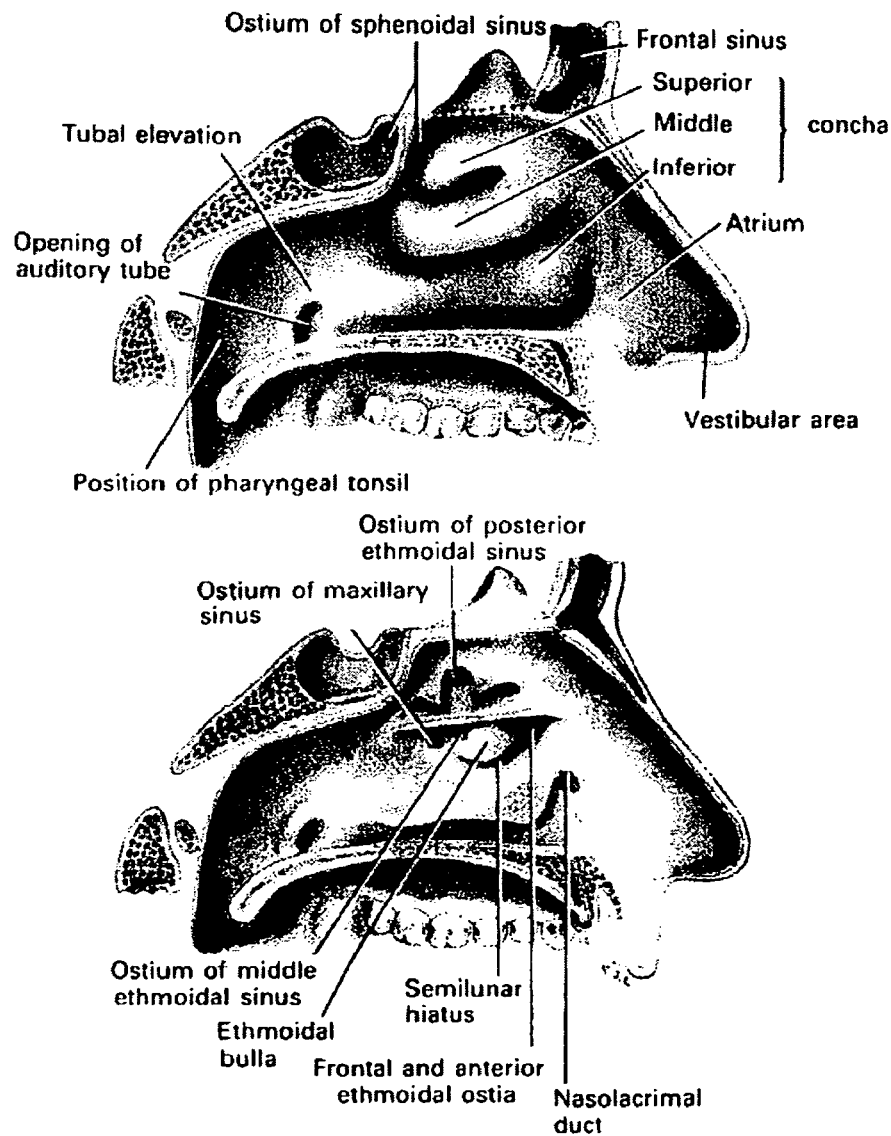
FIG. 3 depicts the internal anatomy of the nasal cavity and the lower opening of the nasolacrimal duct.

FIG. 3 shows the internal anatomy of the nasal cavity and the point of entry of the nasolacrimal duct. Excess fluid (tear or irrigate) in the conjunctival sacs is drained through the nasolacrimal duct, without spilling out, unless it exceeds the drainage capacity. Blinking the eyes pumps the irrigate into the lacrimal sacs through the bilateral paired (upper and lower) lacrimal puncta atop the lacrimal papillae at the medial (inner) ends of the eyelids, into the short lacrimal cannaliculi, which connect with the lacrimal sacs. The fluid then enters the one-way nasolacrimal ducts and down through the lower openings of the ducts, into the nasal cavity, beneath the inferior meatuses, two centimeters behind the nostrils. With the patient semi-inclined, the fluid runs back into the posterior nasal cavity, enters the nasopharynx, and moisturizes the nasopharyngeal mucosa, loosening the secretions. The nasopharyngeal secretions and tear or irrigate then proceed down into the oropharynx, and elicit a sensation of fluid in the back of the throat. When this occurs, the patient will have the urge to swallow the fluid. Patients are instructed to spit the fluid into the specimen container instead of swallowing it. Patients with an intact sense of taste for salt, and in the absence of overwhelming taste from other recently ingested material, generally can appreciate the salty taste of the fluid (if physiologic saline is used as an irrigate) as it is expectorated.

FIG. 4 is the English version of explanatory notes given to patients, to help them collect the CURTI specimens.

Figure 5B:
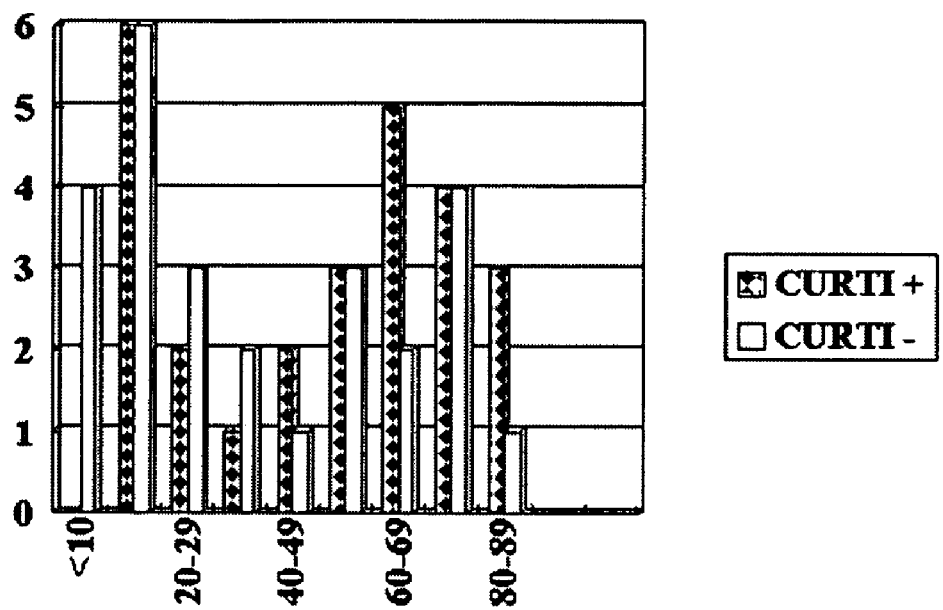
FIG. 5 tabulates the results of CURTI in a series of patients with influenza A infections.

FIG. 5A shows the performance of CURTI when evaluated after a short delay (within 24 hours) in patients with confirmed influenza A infection (by DIF). Positivity by CURTI is defined as positive identification of influenza A virus by viral culture or positive identification of influenza A infected epithelial cells by DIF. Only 50% of the patients were positive by CURTI because not all specimens were cultured for virus; some patients cannot perform CURTI, namely children younger than 10 years old (FIG. 5B); and rapid elimination of influenza A by the patients immune system owing to the delay in performing CURTI. Many or most patients admitted into hospital for influenza A infection are young children or elderly institutionalized patients identified after an outbreak of influenza A infection. Because of delay in recognition and admission, some patients are on the verge of clearing the virus, or have commenced antiviral agents following the diagnosis of influenza A infection. Further delay in performing CURTI may explain some of the "false negative" results with CURTI. Other possible reasons include anatomical abnormalities precluding the entry of conjunctival irrigate into the nose, inattention to detail, or insensitivity of existing laboratory methods of viral identification.

DETAILED DESCRIPTION OF THE PRESENTLY PREFERRED EMBODIMENTS

Anatomy

The lacrimal sac is located at the medial corner of the eye, deep in the medial palpebral ligament and some of the muscle fibers that shut the eyelids (palpebral fibers of the orbicularis oculi). It is a dilatation of the blunt upper end of the nasolacrimal duct, and is connected to the conjunctival sac (the space between the eyelids and the eye) via two short cannaliculi (narrow ducts). The openings or puncta of these lacrimal cannaliculi into the conjunctival sac can easily be seen on the medial aspects of the upper and lower eyelids atop two small papillae, called the lacrimal papillae (FIG. 2). The lower end of the lacrimal sac continues as a thick-walled tube with mucosal folds that only permit one-way traffic of tears—down into the nose. This tube is the nasolacrimal duct. It is about 2 cm long, and slopes downwards and outwards along the outer wall of the front of the nasal cavity, and open into a recess called the inferior meatus.

When excess tear enters the conjunctival sac, owing to increased secretion, the tear does not normally spill because of the lid margins, which repel water due to the oily secretions of the Meibomian glands. Instead, blinking occurs and assists the drainage of tear into the lacrimal sac. This occurs because during blinking, the lacrimal puncta turn inwards to face the lacus lacrimalis, the space just internal to the puncta. Simultaneously, muscles that close the eyelids also draw open the lacrimal sac, which is usually collapsed because of its elasticity. Tear is sucked into the lacrimal sac by this action. When the eyelids open and the muscle relaxes, the lacrimal sac returns to its original collapsed state. Its contents are pumped into the nasolacrimal duct, and hence into the nose. Mucosal folds in the lacrimal duct act as valves, preventing the tear from running back. In this way, a system of valves and pumps direct excess tear from the conjunctival sacs to the nose via the nasolacrimal sac and nasolacrimal duct. When tear enters the nose, it trickles back to the nasopharynx, unless it is blown out of the nose. After running into the nasopharynx, the tear and secretions of the nose and nasopharynx mingle and elicit a sensation of fluid collecting in the throat. Young children might instinctively swallow it. Adults can be instructed to refrain from swallowing it and instead spit it out. These processes form the anatomical basis of this invention.

The Method of CURTI (Conjunctivo-Upper Respiratory Tract Irrigation)

In order to collect nasopharyngeal cells (exfoliated epithelial cells, and immune cells that migrate into the secretions), or other material present in the nasopharynx, such as viruses, or cancer cells, this invention takes advantage of the anatomical properties previously described. We employ sterile physiological saline solution to produce excessive artificial tears that irrigate the nasopharynx, and hence produce a collection of fluid with admixed cells and secretions that can be spit out. Other methods include stimulation of tear secretion by topical eyedrops, eliciting emotions, and irritating fumes or vapor. In the kinder method of this invention, the saline provokes no unpleasant sensation, because it is at the same room temperature as the eyes, of the same osmolality, pH, and contains no preservative or other chemicals that irritate the eyes. Because of this, physiological saline does not cause the patient to "screw-up" the eyes (forcibly shutting the eyelids), thereby preventing the irrigate from spilling out onto the cheeks. The amount of irrigate is also completely under the control of the patient.

To successfully practice this invention, the patient needs to understand the procedure as follows:

1. The procedure can be performed by the patients on themselves. Patients should be seated or semi-reclined in a comfortable and safe chair or couch, in a room without bright lights on the ceiling.

2. The provided sterile physiologic saline is to be instilled into both eyes while the patient sits with his or her face towards the ceiling, in order to avoid spilling.

3. Only one drop per eye is to be applied at a time.

4. The patient should then hold his/her head facing forward (erect or semi-erect) to help drainage of the fluid into the lacrimal sac.

5. The patient should not forcibly close the eyes, because the solution will run out of the eyes if they are forcibly closed.

6. Both eyes should be blinked normally a few times, until the sensation of fluid in the eyes is almost gone.

7. Next, the patient should repeat the application of the physiological saline eye drops and the eye-blinking, until all 2-5 ml of physiologic saline is used up.

8. A minute or two after beginning the application of the eye drops, the patient will feel fluid entering the nose. This lag phase is to be expected.

9. The patient should tilt the head backwards slightly to facilitate the fluid to drain into the back of the throat when fluid enters the nasal cavity.

10. A sniffing action will help the fluid run back.

11. When sufficient fluid has collected at the back of the throat, i.e. not as soon as fluid runs into the throat, the patient should spit the fluid out into the provided sterile, RNAse (ribonuclease)-free, and DNAse (deoxyribonuclease)-free specimen container. This delayed spitting ensures minimal dilution of the specimen by saliva.

12. Special emphasis should be made to ask the patient to refrain from swallowing the fluid.

13. After using up the provided physiological saline, fluid will continue to run into the nose and back of the throat for a minute or two. This fluid should also be collected into the specimen container.

Other instructions to the patient should include avoiding foods and drinks with a strong taste, immediately before the procedure, as well as avoiding cigarette smoking. This helps the patient sense the salty taste of the spit. In addition, it helps to ask the patients to rinse their mouths with water first, and to thoroughly wash their hands, so that they can gently massage the region of the lacrimal sac (the inner corner of the eye) to help open it up for the fluid.

Because it generally requires previous experience with using eyedrops, this invention is recommended for adults and older children. Young children who have had no prior experience need to rehearse and be educated prior to the actual procedure. For most other patients, a detailed written instruction in the language of the patient is sufficient (FIG. 4).

Specimen Container, Specimen Preservation, and Transport

The container used for specimen collection is preferably a wide-mouthed sterile bottle with an O-ring at the lid to make it leak-proof upon screwing on. It should be free of RNAse and DNAse. A line or engraving on the bottle near the bottom indicates the amount of specimen that will be sufficient when the meniscus level of the collected fluid reaches it.

Depending on the analyte, cells, or pathogen sought, the specimen is best kept at room temperature or 4° C., prior to handling in the laboratory. For virus studies that involve cultivation of virus in cell cultures, it is important to adequately preserve the virus and inhibit the proliferation of bacteria, by transferring a small aliquot (about 200 microlitres) into a virus transport medium. For extraction of labile molecules, such as mRNA (messenger RNA), lysis buffer should be added to an aliquot at the earliest convenience, generally within a few hours of collection for a specimen that has been promptly put into the 4° C. compartment of a refrigerator. To prevent the overgrowth of oral commensal organisms in an aliquot that will be cultured for bacteria, other chemicals, such as antibiotics, can be added. Fixatives such as ethanol or formalin can be added if the specimen will be used for cytological examination.

The usual precautions of screwing the cap securely, bagging to prevent leakage and endagerment of messengers and laboratory workers, as well as proper identification and labeling of the specimen bottle, should be observed.

Quality Control and Assurance

The specimen is whitish and frothy, resembling saliva, as it is mixed with saliva. For patients with purulent infection of the nasal cavity or nasopharynx, the specimen may have a yellowish or greenish tinge. Blood stain is not normally expected, but if it is present, it should be noted. For patients with an intact sense of taste for salt, and who had rinsed their mouth with water prior to the procedure, the spit should taste a little salty. In fact, the nasopharynx has taste buds for salt (personal observation). Tasting salt in the spit is a quality-assurance observation that should be asked of every patient, although its absence does not necessarily indicate inadequacy of the specimen. Other observations that suggest that the specimen is adequate include the patient's recount of fluid entering the nose and throat and successful expectoration of the fluid into the container. Other methods of quality assurance is listed below.

Methods to Ensure Adequacy of Specimen therefore Include:

1. Reporting the taste of salt in the nasopharynx or spit, or the sensation of fluid running through the nose and into the throat, is an indication of an adequate specimen. If preservatives or indicators (such as fluorescein) are present in the eye drops used for CURTI, they will generally give a bitter taste. If dextrose water is used instead of physiologic saline, the patient will experience a sweet taste. Solutions containing metabolizable carbohydrates should however, be avoided, as they may trigger bacterial growth. These taste sensations can be used as quality assurance observations.

2. Inclusion of an indicator solution in the eye drops. An example is fluorescein, whose presence can readily be detected by viewing the specimen under Wood's light (Long UV or UV-A, wavelength 320 to 380 nm). Ophthalmologists routinely use fluorescein (eye drops or strips) on patient's eyes to detect corneal ulcerations.

3. Measuring the pH of the spit. In healthy people, the pH of saliva is the same as extracellular fluid, or about 7.4. The pH of normal saline is 7.0 (neutral). However, it can be affected by dental caries, foods and drinks, medications and other factors. Measuring the pH before and after the procedure can indicate if there is any change in pH caused by the instillation of physiologic saline on the patient's saliva—a measurable change, for example, a change from 7.4 to 7.1, is an indication that the specimen is adequate.

4. In the laboratory, the presence of diagnostic material is an indication that the specimen is adequate. Diagnostic material can be columnar cells containing fluorescent nuclei when stained with an appropriate fluorescein-labeled antibody. Diagnostic material can also be molecular markers of cancer, or cytologically atypical cancer cells. Squamous cells will be present in abundance, as they normally are in the saliva, and have no significance. On the other hand, columnar cells are normally rare, and their absence does not prove the inadequacy of the specimen.

Modifications of CURTI

Some patients may not be able to perform the entire procedure of CURTI by themselves. These patients will need assistance by medical or nursing personnel. This generally amounts to holding the syringe (or bottle) containing the physiologic saline and/or the specimen bottle for them when required, applying eye drops for them, assisting them in sitting up to spit the fluid, the positioning of the specimen container close to the mouth, making sure the patient is doing the procedure correctly, ensuring sufficient specimen is collected, making sure the specimen does not spill, and making sure that the specimen container is adequately closed at the end of the procedure. Patients requiring such forms of assistance have included mildly mentally handicapped patients and bed-ridden elderly patients. Other patients who might need such forms of assistance might include young children, patients who are visually compromised, seriously injured or ill patients, or patients who do not have full use of one or both upper extremities.

Even in these circumstances, CURTI is preferred over nasopharyngeal wash or other methods whenever possible, even if assistance is required, because patients find it much gentler than nasopharyngeal aspiration. Patients also do not sneeze or cough, and are more likely to agree to repeated collections for additional or follow up studies.

All-Containing Kit

Thus this invention is best practiced in the form of a kit including: bottled sterile eye drops with or without indicator (with expiration date), leak-proof specimen container with marking indicating adequacy of volume and label for patient to print his or her name, leak-proof plastic bag to contain specimen and any leakage, instruction sheet, and the appropriate additive(s) (to be added to the specimen after collection). If the kit is to be used at the patient's home, an appropriate questionnaire asking such questions as name and contact information, brief clinical history, whether patient tasted salt (if used as quality assurance measure), and date and time of collection; and further instructions regarding how and where to submit the specimen, and return address, etc., will be included.

EXAMPLES

1. Collection of Nasopharyngeal Specimens for SARS Diagnosis.

In Spring of 2003, an outbreak of SARS occurred in Hong Kong. Towards the end of the outbreak, this invention was first tested on four recently admitted SARS patients.

All four patients had nose and throat swabs for molecular diagnosis of SARS by RT-PCR. Nasopharyngeal aspiration was not performed because of the fear of contracting SARS from patients. These patients were confirmed to have SARS by subsequent seroconversion to SARS coronavirus or by positive liver biopsy (RT-PCR) for the virus.

None of the nose and throat swabs were positive. In addition, stool was collected for RT-PCR, because it became known that significant numbers of SARS patients excrete the SARS coronavirus in the stool. However, none were positive in the four patients.

CURTI was performed for all four patients. Two patients were positive. This invention thus provided much better specimens compared with throat and nose swab. It does not put medical personnel at extra risk of contracting the lethal viral infection because the patients performed the entire procedure themselves. Compared with seroconversion, molecular diagnosis of SARS by RT-PCR offered a specific diagnosis of SARS at a much earlier stage.

2. Collection of Nasopharyngeal Specimens for Diagnosis of Influenza

Influenza A virus is an RNA virus whose natural host is the water fowl. When it infects chickens, the mortality is extremely high. Human beings and pigs are also susceptible to infection. Pigs are well known as "mixing vessels" for viral recombination between bird and human strains of influenza A viruses. Recombination creates new influenza A viruses with antigenic shift. When humans encounter them, their immune system memories do not recognize the new viruses, consequently taking longer to respond and giving the virus enough time to cause clinical illness and to spread itself to many more susceptible hosts. Because influenza A is highly infectious, requiring as little as three viral particles to cause infection, and because it is most often transmitted by droplets and aerosol, outbreaks frequently occur in institutions, and hospitals. Rapid diagnosis, leading to quarantine and isolation of infected patients, is dependent on a way of reliably collecting clinical specimens.

This invention provides a high-yield, comfortable, and safe (to medical personnel) method of specimen collection for laboratory diagnosis of influenza A infection. Specimens collected can be tested by any of the commonly used techniques, including the point-of-care Enzyme Immuno-Assay (EIA), BD DIRECTIGEN™ Flu A, the slower but more widely available method of Direct Immunofluorescent Microscopy (DIF), virus culture, and the increasingly speedy and by far the most sensitive and specific method of RT-PCR.

In a partially published series (reference 11) of 52 patients who were diagnosed by DIF to have influenza A infection and retested by the same laboratory method of DIF on CURTI specimens within 24 hours, 26 were found to be positive (FIG. 5).

Under the fluorescent microscope, a smear of the specimen that has been pre-incubated with fluorescein-labeled influenza A-specific antibody shows bright green fluorescence of the nuclei and cytoplasm of infected ciliated columnar epithelial cells. The nucleus is oval and located at the base of the cell. In the two cases, these cells were present in sufficient numbers to permit easy identification among contaminating, non-autofluorescent squamous cells, which were much larger. In addition, cellular debris was not excessive enough to obscure the identification of diagnostic virally infected cells.

3. Collection of Nasopharyngeal Specimens for Diagnosis of other Upper Respiratory Viral Illnesses, such as Influenza B, Parainfluenza, Metapneumonia Virus, Rhinovirus, Coronavirus, Respiratory Syncytial Virus, Herpes Simplex Virus, and Adenovirus.

DIRECTIGEN™ Flu B test is a point-of-care antigen detection system similar to the DIRECTIGEN™ Flu A test. It specifically identifies influenza B and is marketed in combination with DIRECTIGEN™ Flu A as DIRECTIGEN™ Flu A+B. DIRECTIGEN™ RSV Test detects respiratory syncytial virus. Similar tests against other upper respiratory viruses are being developed or in the planning phase. All these are readily coupled to this invention for maximal patient comfort, specimen quality, and safety to staff.

4. Coupling this Invention in a Diagnostic Kit with Nucleic Acid Amplification, such as PCR-EIA, or RT-PCR.

Nucleic acid amplification is fast becoming the preferred method of amplifying a viral "signature" without the attendant risk of producing complete infectious viruses. In addition, it has remarkable sensitivity unrivalled by any antigen-based tests. With the automation afforded by Real-time quantitative PCR, the entire process of nucleic acid amplification takes less than one hour. In addition, the technology permits measurement of the concentration of the virus in the specimen.

Most methods of collection of nasopharyngeal material utilize large amounts of irrigate, or depend on a solution to harvest swabbed cells. The quantity of viruses obtained do not therefore reflect the true amount of viruses present, although with standardization of the technique, meaningful results still emerge by comparison between patients. This invention provides a small amount of irrigate, which rather than flushing out the virally infected cells, causes moisturization or rehydration of pre-existing mucus (secretions) and their induced discharge. The quantity of virus detected in the CURTI specimen therefore matches more closely the original viral load in the nasopharyngeal secretions.

We have developed an even more sensitive method of nucleic acid amplification, PCR-EIA. This method provides a further layer of signal amplification of the PCR product using enzyme immunoassay.

5. Collection of Nasopharyngeal Secretions for Screening for Nasopharyngeal Cancer.

Nasopharyngeal cancer is prevalent in certain parts of the world, including Southern China. It is caused by clonal proliferation of transformed nasopharyngeal epithelial cells that acquire immortality, uncontrolled cell proliferation, invasiveness, and the ability to metastasize to distant sites. Many cases have residual evidence of prior EBV (Epstein-Barr virus) infection, suggesting that the virus is the initial transforming event. Because the nasopharynx is located in the center of the head, is inaccessible to visual inspection or palpation by the patient, and tumors that originate there produce little initial discomfort. Most cases present at a late, incurable stage.

Until now, there has been no effective method for screening such patients without invasive and costly nasopharyngeal endoscopy. This invention provides a comfortable and reliable means to collect exfoliated nasopharyngeal cells or molecular/viral markers for examination. Such specimens will need to be immediately processed or fixed to provide the best preservation of molecular markers or morphological details for microscopic examination.

This invention also provides specimens for molecular screening and diagnosis of nasopharyngeal carcinoma and other malignancies affecting the nasal cavities, nasopharynx and oropharynx, using microsatellites, telomere and telomerase-related markers, promoter hypermethylation, global genomic hypomethylation, tumor suppressor gene inactivation, oncogene activation, aberrant pattern of expression or suppression of genes and other markers, chemical profile, mucosal secretory IgA specificities and viral markers (such as Epstein-Barr viral antigens and nucleic acids).

6. CURTI as a Method of Vaccine Delivery.

Some vaccines are delivered parenterally (not through the mouth). Others, such as the oral polio vaccine (Sabine vaccine), is delivered enterally (by mouth). This live attenuated (weakened) oral polio vaccine (OPV) was developed by Dr. Albert Sabin in 1961. The advantage over the Salk vaccine, which is an inactivated (killed) polio vaccine (IPV)—developed in 1955 by Dr. Jonas Salk—is that IPV has to be injected by a trained health worker. Other benefits to OPV include longer lasting immunity and mucosal immunity, because polio virus enters the body through the mouth.

CURTI is therefore a preferred method to administer live attenuated vaccines against upper respiratory viral illnesses, which generally gain access to the body via the upper respiratory tract, including the eyes. Delivery may be performed by positioning the patient with his/her face pointing upwards, and dropping the fluid containing the vaccine into the eyes.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method of collecting and testing nasopharyngeal specimens comprising the steps of: 1) positioning the patient with his or her face pointing upwards, 2) dropping at least a single drop of a sterile solution into each eye at a time and then holding head erect and blinking several times, 3) repeating step 2 until about 2-5 mL of solution has been used up, 4) having the patient spit out the collected fluid in the back of the throat into a specimen container, and 5) testing the collected fluid for a disease or disorder selected from the group consisting of viral upper respiratory infections and malignancies of the nasal, nasopharyngeal, and oropharyngeal regions.

2. The method of claim 1, wherein the viral upper respiratory infection is SARS coronavirus infection, influenza A virus infection, influenza B virus infection, parainfluenza virus infection, coronavirus upper respiratory infection, adenovirus upper respiratory infection, rhinovirus upper respiratory infection, respiratory syncytial virus infection, metapneumovirus infection or other emerging viral infections.

3. The method of claim 1, wherein the malignancy of the nasopharyngeal region is nasopharyngeal cancer.

* * * * *